United States Patent [19]

Kloehn et al.

[11] Patent Number: 4,650,532
[45] Date of Patent: Mar. 17, 1987

[54] METHOD AND APPARATUS FOR MAKING A CURVED HEM ON A MOVING WEB OF FABRIC

[75] Inventors: Kurt J. Kloehn, Outagamie County; Kevin G. Dolan, Winnebago County, both of Wis.

[73] Assignee: Kimberly-Clark Corporation, Neenah, Wis.

[21] Appl. No.: 709,964

[22] Filed: Mar. 11, 1985

[51] Int. Cl.$^4$ .............................................. B31F 1/00
[52] U.S. Cl. ...................................... 156/204; 29/512; 156/227; 156/252; 156/443; 156/459; 156/513
[58] Field of Search ............... 156/212, 216, 226, 227, 156/252, 443, 401, 478, 479, 486, 204, 513, 253; 29/512, 523; 112/68, 264.1; 277/235 B; 428/121, 124, 127–129, 131, 133

[56] References Cited

U.S. PATENT DOCUMENTS

| | | |
|---|---|---|
| 3,018,518 | 1/1962 | Jefferys ............................ 156/401 X |
| 3,475,249 | 10/1969 | Smith ................................ 156/253 |
| 3,587,501 | 6/1971 | Cruden ............................. 112/264.1 |
| 3,694,889 | 10/1972 | Pommier ...................... 277/235 B X |
| 3,756,878 | 9/1973 | Willot ............................. 156/253 X |
| 4,155,798 | 5/1979 | Becker ............................... 156/216 |

Primary Examiner—David Simmons
Attorney, Agent, or Firm—John L. Chiatalas; Donald L. Traut

[57] ABSTRACT

A method of forming folded hems about the periphery of openings in a moving fabric web includes inserting a mandrel having radially expandable and contractible folding means into the openings to turn out of the web a peripheral portion of the fabric which is then folded back by radial expansion of the folding means. The folding means is radially contracted for entry and withdrawl of the mandrel. Apparatus for carrying out the method may comprise a rotating drum within which a plurality of mandrels is mounted to orbit with the drum. A continuous web of fabric having openings therein is carried by the drum and positioning means reciprocatingly insert and withdraw the mandrel through the fabric openings. Control means radially expand and contract the folding means synchronously with the positioning means.

18 Claims, 12 Drawing Figures

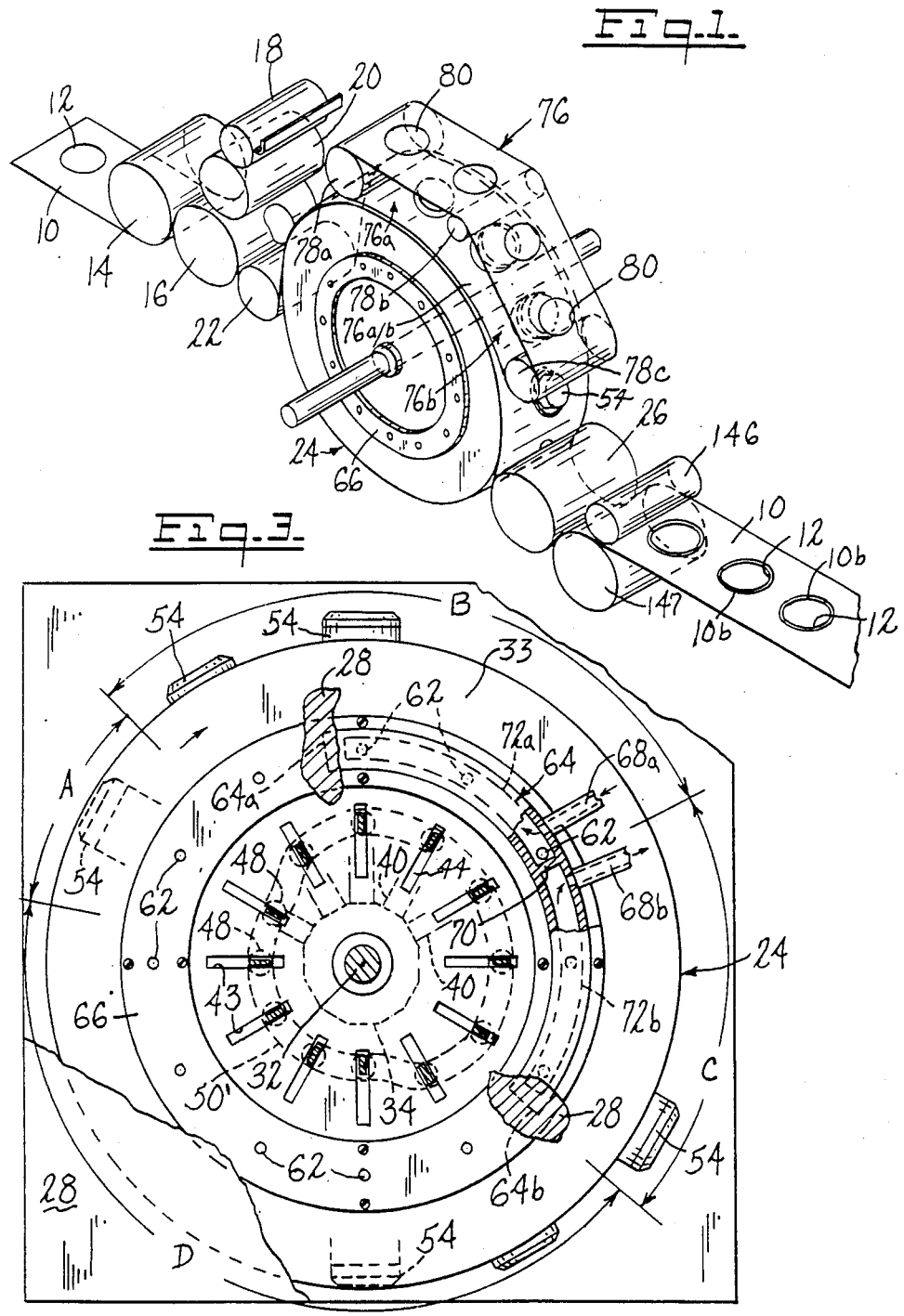

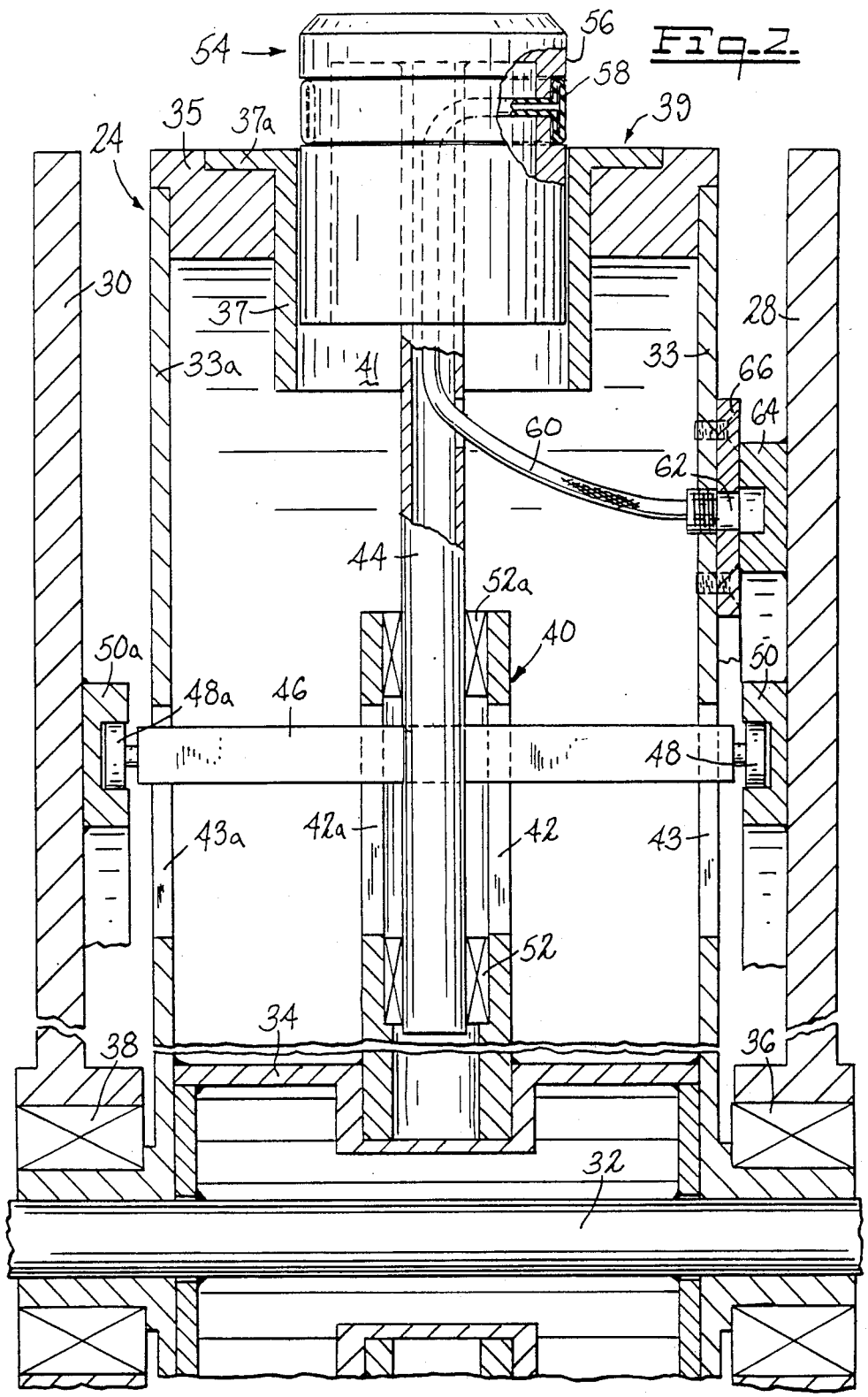

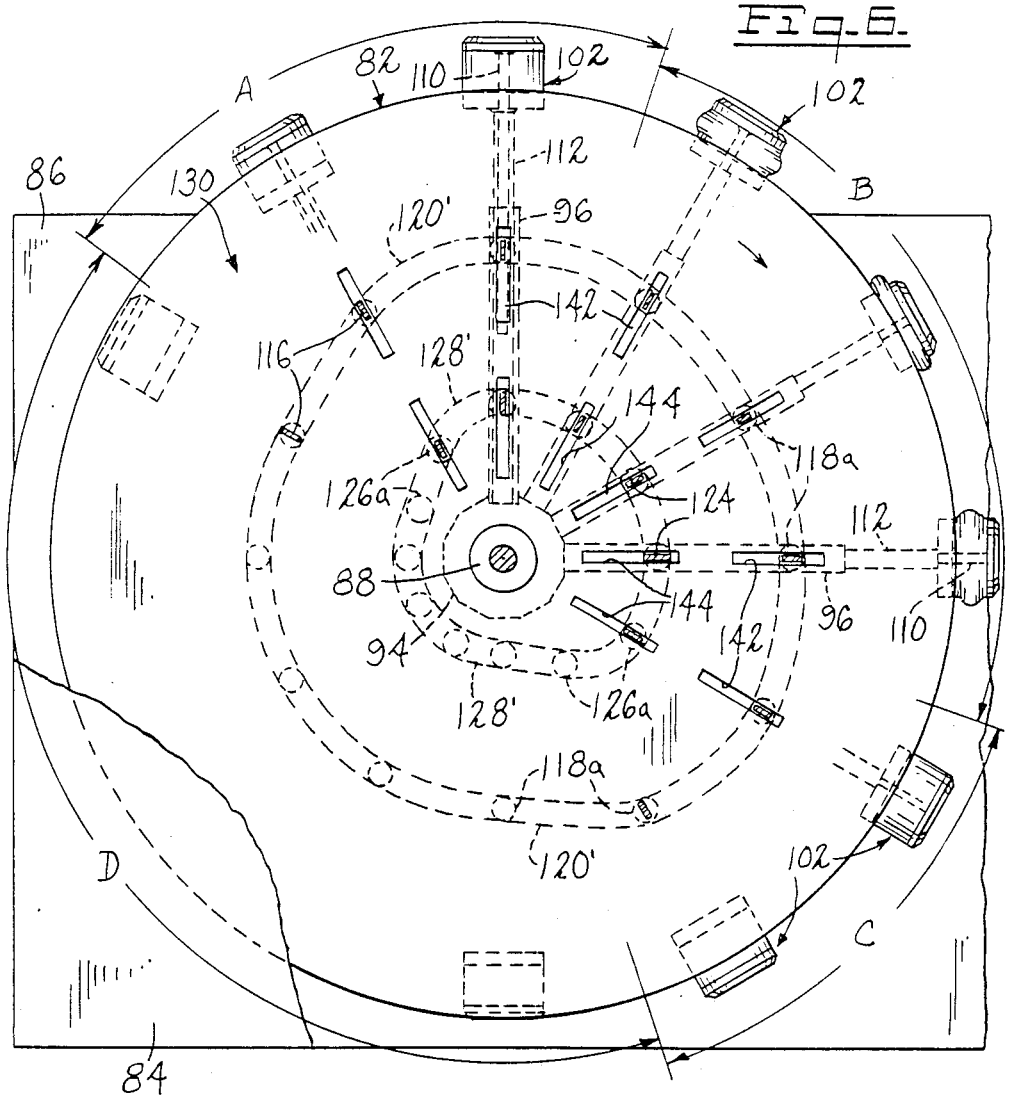

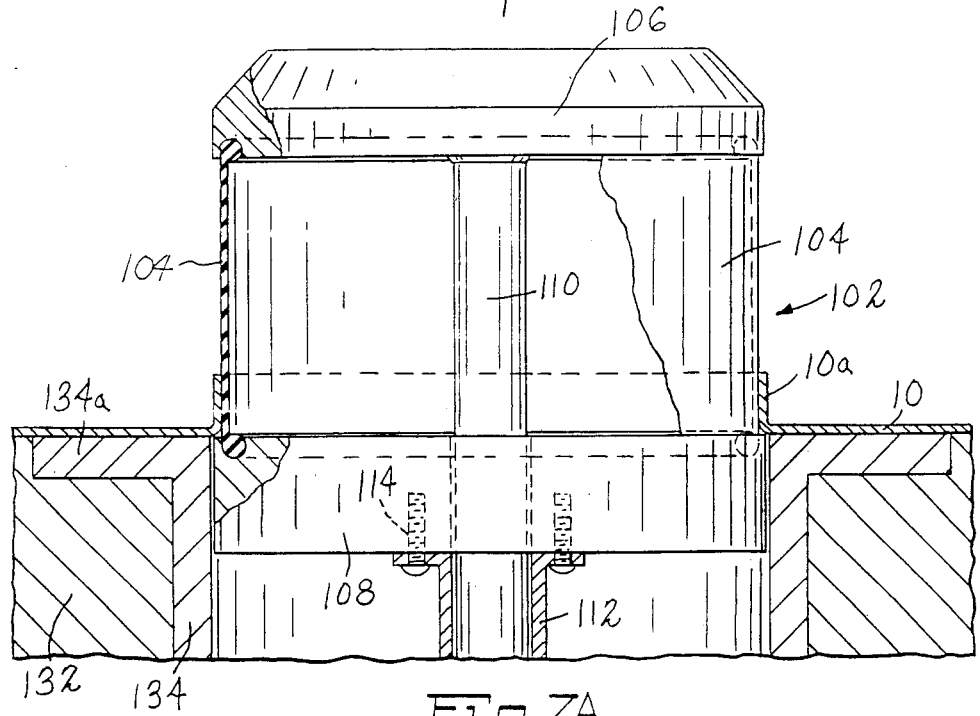
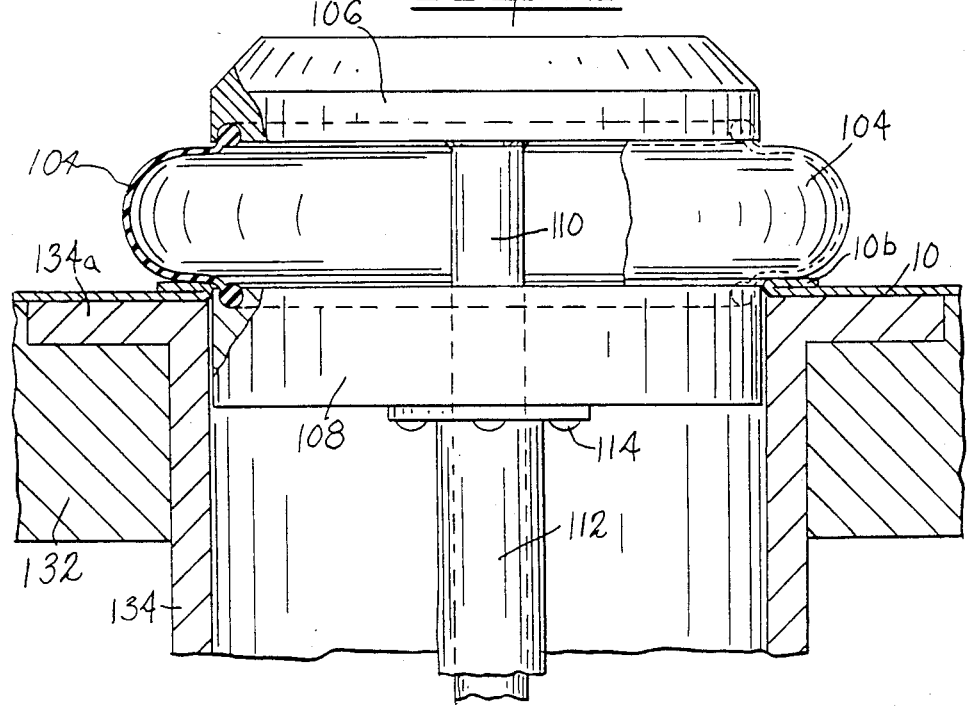

METHOD AND APPARATUS FOR MAKING A CURVED HEM ON A MOVING WEB OF FABRIC

BACKGROUND OF THE INVENTION

The present invention concerns a method and apparatus for making curved hems about the periphery of respective openings in a moving web of fabric, such as a web of material employed in the manufacture of disposable diapers. The modern manufacture of items such as disposable diapers usually employs continuous moving webs of materials, such as non-woven fabrics, moving at high speeds, for example, linear speeds of 600 feet per minute. The high web speeds necessary for efficient manufacture make it difficult to form hems about openings cut in the web.

SUMMARY OF THE INVENTION

In accordance with the present invention there is provided a method of forming folded hems about the periphery of respective openings in a moving fabric web by utilizing at least one mandrel having a radially expandable and contractible fabric folding means, wherein the method comprises: moving a continuous web of fabric having a plurality of openings therein into a hemming station and therein inserting the mandrel into respective openings from one side of the fabric for a distance sufficient to turn out of the web a peripheral portion of the fabric adjacent the respective openings and to position the fabric folding means in folding alignment with the turned out portion; radially expanding the folding means while it is positioned in said folding alignment whereby the turned-out portion of the fabric is pressed into contact with the other side of the fabric web to form the hem; radially contracting the fabric folding means and then withdrawing the mandrel from the opening; and securing the hem in place and withdrawing the moving web from the hemming station.

Yet another aspect of the invention comprises supporting the fabric web on a fabric support means having formed therein at least one mandrel passageway of a diameter less than the diameter of respective ones of the openings, positioning the fabric web on the fabric support with at least one of the openings aligned with the mandrel passageway, and inserting and withdrawing the mandrel through the mandrel passageway and the opening aligned therewith while the fabric folding means is radially contracted.

Another aspect of the invention comprises placing a hold-down member on the fabric web adjacent to the periphery of at least one of the openings to hold the fabric web in place on the fabric support means while the mandrel is inserted into the opening.

Yet another aspect of the invention provides the additional step of passing the moving web into a cutting station and therein cutting the plurality of openings in the web, prior to passing the web into the hemming station.

The present invention also provides apparatus for forming a folded hem about the periphery of an opening in a fabric web, which apparatus comprises: a mandrel having an upper portion, a sidewall comprising a radially expandable and contractible fabric folding means, and a lower portion; mandrel support means on which the mandrel is mounted; fabric support means having a fabric side dimensioned and configured to receive and support a fabric thereon, and further having therein at least one mandrel passageway dimensioned and configured to permit passage therethrough of at least so much of the mandrel as is necessary to position it as defined below; positioning means operatively connected to at least one of the mandrel and the fabric support means to move them relative to each other to reciprocatingly insert and withdraw the mandrel through the mandrel passageway and between (i) a folding alignment position in which the folding means is on the fabric side of the fabric support means, and (ii) a withdrawn position in which the mandrel is clear of at least the fabric side of the fabric support means; and control means operatively connected to the folding means to radially expand the folding means to its expanded position when it is on the fabric side of the support means and to radially contract it for movement through the mandrel passageway.

In a specific aspect of the invention, the positioning means is operatively connected to the mandrel to reciprocatingly insert and withdraw the mandrel through the mandrel passageway.

In one aspect of the invention, the fabric support means comprises a rotating drum carrying a continuous web of fabric thereon and the mandrel is mounted for orbiting with the rotating drum to maintain the mandrel in axial alignment with the mandrel passageway for at least a segment of each revolution of the drum.

In another aspect of the invention, the fabric folding means comprises an expandable and contractible sidewall member of the mandrel connecting the upper and lower portions thereof and the control means comprises a control bar affixed to the upper portion of the mandrel and operatively connected to a control guide arm having thereon a cam follower which engages a control cam track which defines the travel path of the control bar, the control cam track being of eccentric configuration whereby during each revolution of the drum the control guide arm guides the control bar to alternately move the upper and lower portions of the mandrel axially toward and away from each other whereby to alternately radially expand and contract the sidewall member at least once during each revolution of the drum.

In yet another aspect of the invention, the fabric folding means comprises an inflatable bladder of toroidal configuration extending radially about the periphery of the sidewall and the control means comprises means to selectively force a fluid into and withdraw it from the bladder whereby to alternately radially expand and contract the bladder at least once during each revolution of the drum.

Other aspects of the invention are shown in the following description of the preferred embodiments.

BRIEF DESCRIPTION OF THE DRAWINGS

FIG. 1 is a schematic perspective view of one embodiment of apparatus useable in practicing the present invention, with parts omitted and broken away for clarity of illustration, the apparatus comprising a rotating drum having a rim support surface over which a continuous web of material is transported, the drum including a plurality of radially reciprocating mandrels;

FIG. 2 is a partial longitudinal section view of the rotating drum of an apparatus of the type illustrated in FIG. 1, wherein the mandrels include mandrel folding means comprising an inflatable bladder of toroidal configuration;

FIG. 3 is a partial section view in elevation of the apparatus of FIG. 2 with parts omitted or broken away for clarity of illustration;

FIG. 6 is a partial section view in elevation of the apparatus of FIG. 5 with parts omitted or broken away for clarity of illustration; and FIGS. 7 and 7A are side elevation views showing operation of the mandrel of the apparatus of FIGS. 5 and 6.

DETAILED DESCRIPTION OF THE PREFERRED EMBODIMENTS

Figure 4:
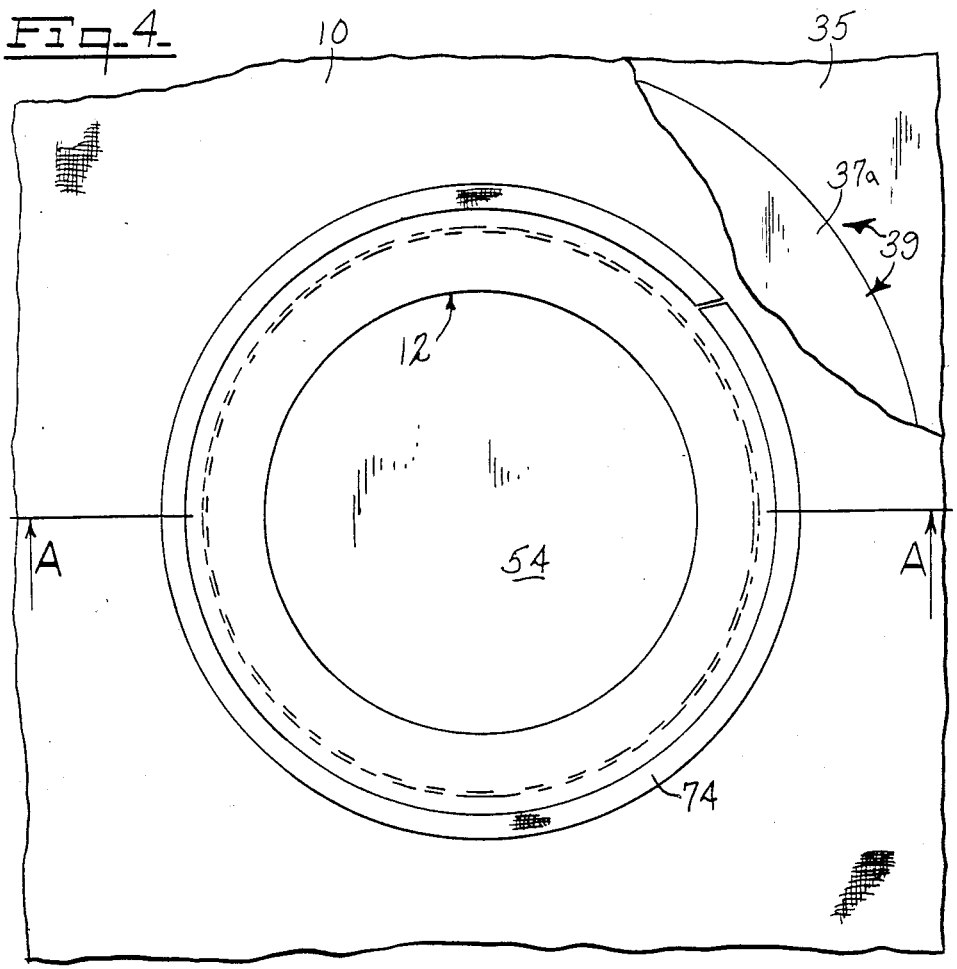
FIG. 4 is a plan view of a segment of the support surface provided by the rim of the drum of the apparatus of FIG. 1.

Generally, in the practice of the present invention, the curved hems are formed about the peripheries of the openings by insertion into each opening to be hemmed a mandrel which includes a folding means to press the hem into place. The present invention provides a significant advantage in providing method and apparatus which enables formation of hems about circular or oval openings or the like while the web is travelling at a high rate of speed, thus permitting utilization of the invention in high speed production lines utilizing continuous moving webs of material. The present invention has particular applicability to the production of garments such as disposable diapers or other incontinence control garments which are typically manufactured by cutting segments from a moving continuous web of fabric. Referring to FIG. 1, a moving continuous web of material 10 has a plurality of openings 12 cut therein in a cutting station (not shown) and is fed by a drive roller 14 through a gluing station comprising a support roller 16, a glue applicator 18 and a transfer roller 20. Glue applicator 18 receives glue from a supply trough (unnumbered) adjacent thereto and is configured to provide the glue in a circular pattern to transfer roller 20 which transfers the glue in a circular pattern about the periphery of each of openings 12. Accordingly, when a hem portion of the fabric around openings 12 is folded back as described below the adhesive will secure the hem in place. The adhesive used is conveniently of the type which will be activated under the folding pressure to secure the hem in place. The adhesive may be omitted and the hem secured in place by any suitable means, using heat, pressure, mechanical or ultrasonic stitching or a combination thereof. Continuous web 10, with the adhesive applied in a pattern about the periphery of openings 12 therein, is guided by feed roller 22 onto the rim of rotating drum 24 and traverses about three-quarters of the periphery of rotating drum 24 before being taken off by take-off roller 26.

An endless belt 76 is driven on a series of rollers 78a, 78b and 78c so as to bear upon continuous web 10 to provide a hold-down section or member 76a which holds web 10 firmly against drum 24. Hold-down section 76a is comprised of that portion of endless belt 76 which initially engages continuous web 10 during a portion of its travel over the support surface provided by the rim of drum 24. A guide section 76b is provided by that portion of endless belt 76 which is downstream (as sensed in the direction of drum rotation) of section 76a. As described below, section 76b, unlike section 76a, is spaced a small distance from continuous web 10 for reasons to be explained. An intermediate portion of belt 76 is designated 76 a/b and represents that portion of belt 76 moving from its hold-down position to its guide position. Endless belt 76 has a plurality of belt openings 80 formed therein which are dimensioned and configured to be aligned with mandrel passageways formed in rotating drum 24 so that the distal ends of mandrels 54 may pass through the hold-down section 76a and guide section 76b of endless belt 76.

Referring to FIGS. 2 and 3, rotating drum 24 is mounted between a pair of opposed machine frames 28, 30 by means of a central shaft 32 and a hub 34, central shaft 32 being mounted in a pair of journal bearings 36, 38 mounted, respectively, in machine frames 28, 30. Rotating drum 24 comprises a pair of opposed generally disc-shaped sidewalls 33, 33a, the respective outer peripheries of which are joined by a circular rim portion 35 which contains therein a plurality of peripherally spaced-apart cylinder sleeves 37, the interiors of which define respective mandrel passageways 41. A series of radially disposed slots 43, 43a are provided in, respectively, sidewalls 33 and 33a of drum 24.

The outer surfaces of rim portion 35 and shoulder segments 37a of cylinder sleeves 37 are dimensioned and configured to cooperate to provide a smooth cylindrical support surface 39 of drum 24. As will be appreciated from FIGS. 1 and 3, the resulting support surface 39 is wide enough to receive and support the moving continuous web 10 fed thereto and has a plurality of mandrel passageways 41 defined by the inner surface of respective cylindrical sleeves 37. Mandrel passageways 41 are disposed at equidistant intervals about rim 35 and extend radially with respect to drum 24.

As best seen in FIG. 3, hub 34 is polygonal in radial cross-section, providing a plurality of faces on each of which (FIGS. 2 and 3) is mounted a respective sleeve 40 which receives a sliding position bar 44 which is connected to a position guide arm 46. As shown in FIG. 2, sleeve 40 is provided with a pair of opposed, longitudinally extending slots 42, 42a which are dimensioned and configured to allow for reciprocating radial movement (upwardly and downwardly as viewed in FIG. 2) of position guide arm 46. Slots 42, 42a are aligned with a corresponding pair of the slots 43, 43a in, respectively, sidewalls 33 and 33a of drum 24. Slots 43, 43a are also dimensioned and configured to allow for reciprocating radial movement of position guide arm 46. At the respective ends of position guide arm 46 are mounted a pair of cam rollers 48, 48a which are respectively received within eccentric, closed loop cam tracks 50, 50a mounted upon the inside faces of, respectively, machine frames 28, 30 in facing coaxial relationship with each other. Cam tracks 50, 50a are dimensioned and configured to form mirror images one of the other.

Positioning bar 44 is mounted for sliding movement within and relative to sleeve 40 by a pair of slide bearings 52, 52a affixed within sleeve 40. Upon rotation of central shaft 32, position guide arm 46 is constrained by cam rollers 48, 48a to follow the path of eccentric cam tracks 50, 50a, which are configured to impose a reciprocating motion upon position guide arm 46 and thereby upon positioning bar 44.

The upper end, as viewed in FIG. 2, of positioning bar 44 has mounted thereon a mandrel 54 which, in this embodiment, is a rigid, hollow member having generally the shape of a piston of an internal combustion engine and including a circumferential groove (unnumbered) extending about the sidewall 56 of mandrel 54 and within which is mounted an inflatable bladder 58 of toroidal configuration, as shown in larger scale in FIGS. 4A-4D. FIG. 2 shows bladder 58 in its deflated condition. A pressure/vacuum header 64 is connected to bladder 58 by means of a pneumatic line 60 which is secured by a fitting (unnumbered) to a pneumatic aperture 62 which extends through sidewall 33 of rotating drum 24 and a circular-track wearplate 66 which is bolted to the outside of sidewall 33. Pneumatic line 60 passes through an opening (unnumbered) in positioning bar 44 and extends through the upper (as viewed in FIG. 2) portion thereof to its connection with bladder 58. As shown in FIG. 3, a plurality of positioning bars 44 each having a mandrel 54 mounted thereon are mounted within respective sleeves 40 carried on respective faces of hub 34, each mandrel 54 being slideably mounted within a cylinder sleeve 37 associated therewith and having a respective pneumatic line 60 connected between its bladder 58 and a pneumatic aperture 62 associated therewith, as described above. Accordingly, a plurality of pneumatic apertures 62 are provided in sidewall 33 and wearplate 66 in evenly spaced-apart relationship along the circumference of an imaginary circle concentric with the longitudinal axis of central shaft 32. Pressure/vacuum header 64 is affixed to the inner face of machine frame 28, is U-shaped in cross-section (FIG. 2) and of arcuate configuration (FIG. 3) and overlies a segment of the imaginary circle along which pneumatic apertures 62 lie. Wearplate 66 is dimensioned and configured so that the bearing rims of pressure/vacuum header 64 bear in sliding, sealing engagement against wearplate 66. The opposite ends 64a, 64b (FIG. 3) of pressure/vacuum header 64 are closed so that wearplate 66 seals the interior of header 64 which is divided by an interior partition 70 into a pressure section 72a and a vacuum section 72b (FIG. 3). Pneumatic conduits 68a, 68b (FIG. 3) are connected to header 64 in order to pressurize section 72a and impose a vacuum on section 72b of header 64.

Upon rotation of drum 24 in the direction indicated by the unmarked arrow in FIG. 3, respective ones of pneumatic apertures 62 are transported first into pressurized section 72a then into vacuum section 72b of header 64 in order to inflate and then deflate bladder 58 as described in more detail below.

Figure 4A:
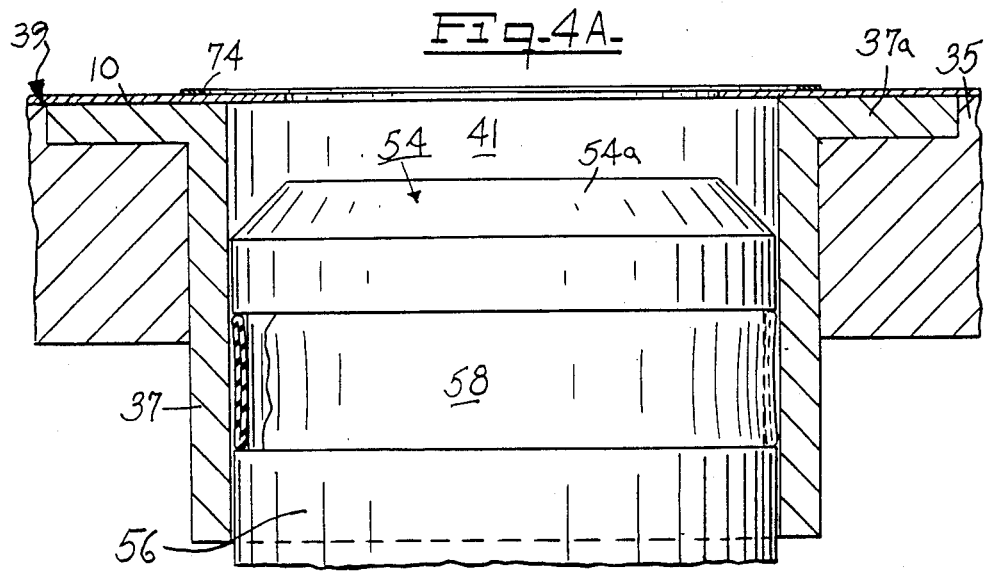
FIGS. 4A-4D inclusively comprise a series of section views in elevation along line A—A of FIG. 4, showing a sequence of operation of a typical mandrel and its associated folding means comprising a part of the apparatus of FIGS. 2 and 3.
Figure 4B:
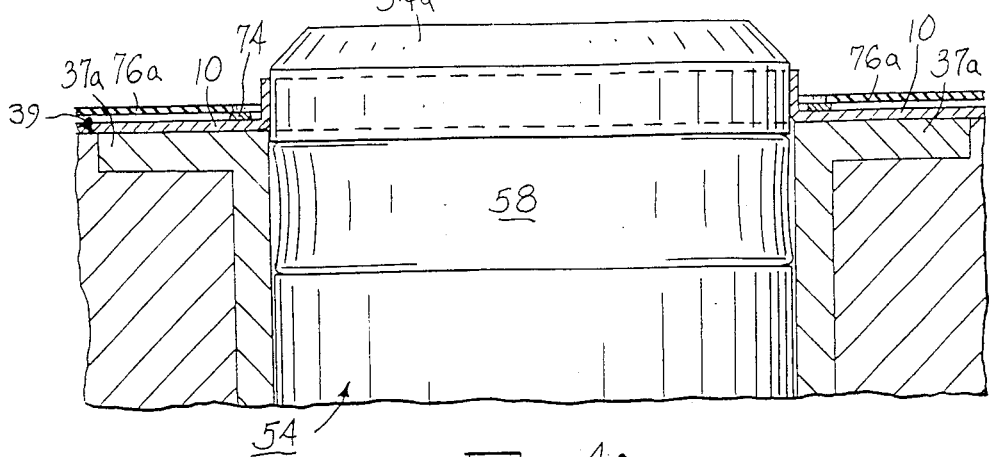
Figure 4C:
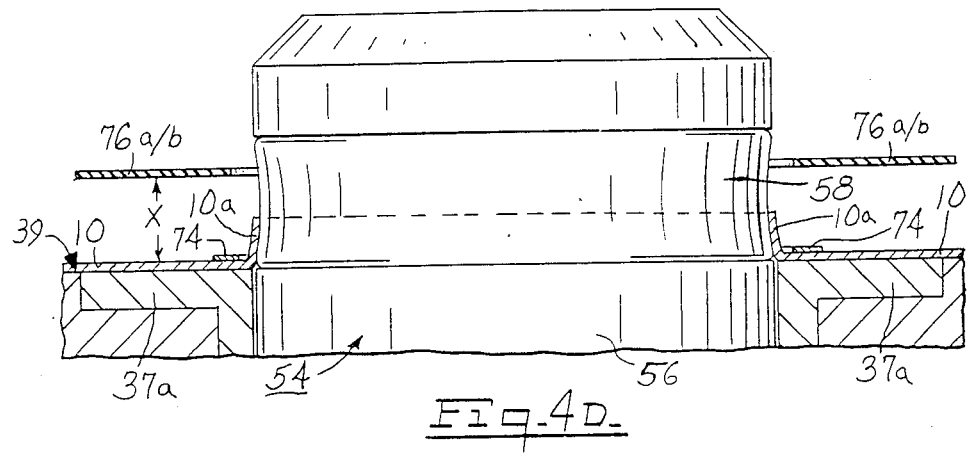

FIG. 3 shows in dotted line the profile 50' defined by the recessed groove of cam tracks 50, 50a (FIG. 2) within which cam rollers 48, 48a (FIG. 2) are constrained to travel by rotation of drum 24. The eccentric configuration of track profile 50' will alternately radially retract and radially advance positioning bar 44, thereby alternately radially retracting and advancing mandrel 54 within its associated cylinder sleeve 37. The position of pneumatic apertures 62, the dimension and configuration of the pressurized and vacuum sections of pressure/vacuum header 64, together with the configuration of track 50' cooperate to coordinate the radial advancing and retracting of mandrel 54 and inflation and deflation of bladder 58 as described below with respect to FIGS. 4-4D. FIGS. 4A-4D show short segments of cylindrical support surface 39 with web 10 supported thereon. The arcuate configuration of support surface 39 is not shown in FIGS. 4A-4D, the illustrated short segments thereof being shown as substantially flat planar segments of the relatively large diameter drum 24. FIGS. 4 and 4A show mandrel 54 in a radially retracted position within cylindrical sleeve 37 and with continuous web 10 overlying support surface 39 consisting of the shoulder 37a of a cylindrical sleeve 37 and rim 35. A typical opening 12 in continuous web 10 has a diameter somewhat smaller than the diameter of mandrel passageway 41 so that a peripheral, annular-shaped portion of the fabric comprising web 10 extends over the periphery of mandrel passageway 41. As shown in FIG. 4A, inflatable bladder 58 is deflated at this point and lies within the circumferential groove (unnumbered) formed in mandrel 54 which, in the embodiment illustrated, has a tapered head portion 54a. A split ring gasket 74 of an elastic material has been deposited by means (not shown) concentrically about opening 12 in web 10 and may be held in place by the circular pattern of adhesive applied about opening 12 as described above. The use of an elasticized gasket 74 is optional and may be employed in those cases where an elasticized hem is to be formed about opening 12. The relative position of mandrel 54 within mandrel passageway 41 provided by cylinder sleeve 37, and the concomitant deflated condition of bladder 58 represents the situation as it exists in Zone A (FIG. 3) of the rotation path of drum 24. As a given mandrel enters Zone B, eccentric track 50' forces cam rollers 48, 48a radially outwardly thereby moving mandrel 54 radially outwardly through cylindrical sleeve 37, as seen by the sequence of FIGS. 4A, 4B and 4C. The tapered portion 54a of mandrel 54 facilitates the engagement and outward pushing of the peripheral edge of the fabric of web 10 by mandrel 54. The peripheral edge portion of fabric is stretched somewhat and folded as it lies along the sidewall of mandrel 54, as seen in FIGS. 4B and 4C.

As mandrel 54 advances outwardly of support surface 39 the turned-out peripheral portion of the fabric of web 10 (FIG. 4B) engages the sidewall of mandrel 54 and hold-down section 76a of belt 76 holds gasket 74 and continuous web 10 firmly in place as mandrel 54 passes through opening 12 and turns out the fabric by forcing the peripheral edge portion of the fabric upwardly, as viewed in FIG. 4B.

Figure 4D:
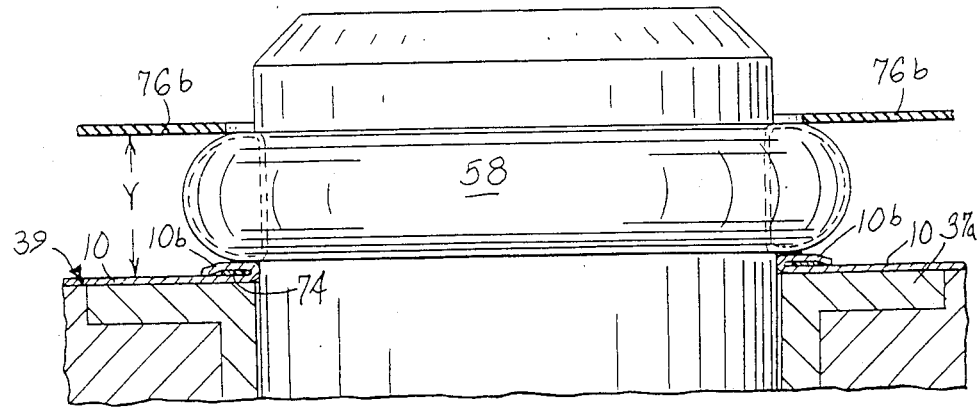

As seen in FIG. 4C, mandrel 54 is advanced radially outwardly sufficiently to place bladder 58 in folding alignment with the turned-out portion 10a of the fabric of continuous web 10. At this point, a section 76 a/b of belt 76 is separating from support surface 39 and web 10 carried thereon and is in an intermediate distance X therefrom moving towards its position relative to support surface 39 and web 10 as shown in FIG. 4D. In FIG. 4D a section of belt 76, designated section 76b, is spaced from support surface 39 and web 10 a distance Y which is sufficient to provide adequate clearance to permit radial expansion of bladder 58. At this juncture, drum 24 has rotated to a position to bring (FIG. 2) the pneumatic aperture 62 which is associated with a given mandrel 54 within pressure section 72a (FIG. 3) of pressure/vacuum header 64, whereby bladder 58 is inflated by pressurized air introduced to it by means of pneumatic line 60 (FIG. 2). During inflation, section 76b of belt 76 provides a guide positioned to help control the direction of inflation of bladder 58 radially outwardly and with sufficient downward force upon the turned-out peripheral edge portion 10a of the fabric of continuous web 10 to insure that, as illustrated in FIG. 4D, the turned-out portion of fabric is folded back onto the top surface of continuous web 10 to provide a 180° fold. Gasket 74 is encased within the hem 10b formed by the folded-back portion. The adhesive earlier applied helps to secure the thus-formed hem 10b in place.

As mandrel 54 leaves Zone B and enters Zone C (FIG. 3) due to the rotation of drum 24, the pneumatic aperture 62 associated therewith enters vacuum section 72b of header 64 and bladder 58 is deflated and radially contracted by the imposed vacuum in order that, as rotation of drum 24 continues through Zone D, mandrel 54 may be radially retracted by positioning bar 44 as cam rollers 48, 48a follow a radially inwardly configured portion of cam track profile 50'. As drum 24 continues its rotation, the cycle is repeated. It will be appreciated that each of the plurality of mandrels 54 goes through the same cycle so that a high rate of forming of the folded hems may be carried out on a continuous web of material moving at high linear speed over rotating drum 24.

FIGS. 5-7A show another embodiment of the invention in which mechanical rather than pneumatic means are utilized to radially expand and contract the folding means associated with the mandrel. In terms of overall construction, the apparatus of FIGS. 5-7A is generally similar to that of the apparatus of FIGS. 2-4, comprising as it does a rotating drum 82 mounted between a pair of opposed machine frames 84, 86 by means of a central shaft 88 carried by a pair of journal bearings 90, 92 which are mounted, respectively, in machine frames 84, 86. The construction of rotating drum 82 is very similar to that of rotating drum 24 of the FIG. 2 embodiment, drum 82 comprising a pair of spaced-apart generally disc-shaped sidewalls 130, 130a joined to a rim portion 132 of cylindrical configuration at the periphery of sidewalls 130, 130a. The outer surfaces of rim portion 132 and of shoulders 134a of cylinder sleeves 134 cooperate to provide a support surface 137. A central portion of sidewalls 130, 130a is joined to hub 94 and thereby mounted for rotation with central shaft 88. A plurality of cylinder sleeves 134 is affixed in equidistant spaced-apart relationship about rim portion 132 and define a plurality of radially extending mandrel passageways 136 within which mandrels 102 are received. Two sets of concentrically disposed and radially extending slots 142, 142a and 144, 144a are provided, respectively, in each sidewall 130, 130a of drum 82. Slots 142, 142a are positioned radially outwardly of slots 144, 144a.

Figure 5:
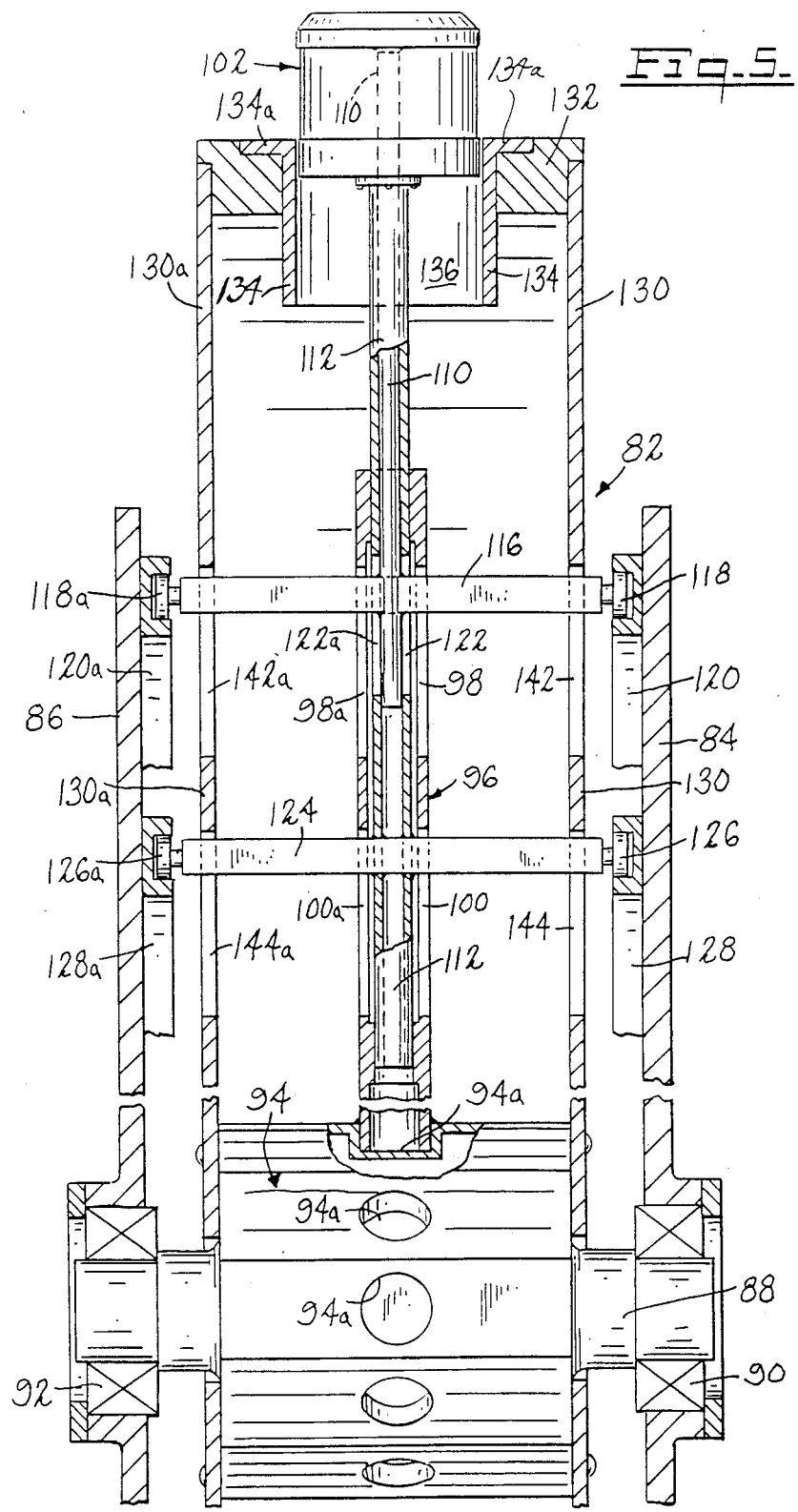
FIG. 5 is a view similar to that of FIG. 2 showing another embodiment of the invention wherein the mandrels include mandrel folding means comprising an expandable and contractible sidewall member of the mandrel.

As in the embodiment of FIGS. 5 and 6, central shaft 88 carries a hub 94 which is polygonal in radial cross-section, each face of hub 94 having an opening 94a which is dimensioned and configured to receive therein a sleeve 96 which has first and second pairs of longitudinally extending slots 98, 98a and 100, 100a formed therein. Each sleeve 96 is received within a respective opening 94a and is welded or otherwise suitably affixed therein. For clarity of illustration, only one of the sleeves 96 and its associated mandrel and cylinder tube is illustrated in FIG. 5, it being understood that an identical sleeve 96 and the parts associated therewith would be mounted in each of the provided openings 94a.

In this embodiment, mandrel 102, as best seen in FIG. 7, comprises a substantially cylindrical shaped expandable and contractible sidewall member 104 which is made of flexible material such as an elastomeric material, and a rigid tapered disc-shaped upper portion 106 and a rigid, disc-shaped lower portion 108. The opposite ends of sidewall member 104 are beaded and seated within a suitably shaped groove in, respectively, upper portion 106 and lower portion 108. In this embodiment, the structure which is equivalent to positioning bar 44 of the embodiment illustrated in FIG. 2 comprises a telescopic bar construction comprising a control bar 110 slideably mounted within a hollow cylinder tube 112. As best seen in FIGS. 7 and 7A, the upper end (as viewed in the Figures) of control bar 110 is affixed to upper portion 106 of mandrel 102 and slideably passes through an aperture (unnumbered) provided at the center of lower portion 108 of mandrel 102. The upper end (as viewed in the Figures) of cylinder tube 112 is affixed by any suitable means such as bolts 114 to the lower end of lower portion 108 of mandrel 102. Referring now to FIG. 5, cylinder tube 112 has a pair of longitudinally extending slots 122, 122a formed therein, control bar 110 near its lower end is affixed to control guide arm 116 which comprises a rigid bar extending through slots 98, 98a and 122, 122a, thence through corresponding slots 142 and 142a in, respectively, sidewalls 130 and 130a. At either end of control guide arm 116 is mounted one of a pair of cam rollers 118, 118a which are received, respectively, within the track profile 120' (FIG. 6) of control cam tracks 120, 120a. The slots through which control guide arm 116 passes are dimensioned and configured to accommodate the radially reciprocating (up and down as viewed in FIG. 5) movement of control guide arm 116.

Cylinder tube 112 is connected to a rigid position guide arm 124 which extends through slots 100, 100a in sleeve 96 as well as through corresponding slots 144, 144a in, respectively, sidewalls 130 and 130a of drum 82. At each opposite end of position guide arm 124 is mounted a cam roller 126, 126a which is received within the recessed track profile 128', of respective position cam tracks 128, 128a. The respective control cam tracks 120, 120a and position cam tracks 128, 128a are mounted on the respective interior facing surfaces of machine frames 84, 86 in a manner similar to that of cam tracks 50, 50a of the FIG. 2 embodiment. That is, cam tracks 120, 120a are coaxially mounted with respect to each other and comprise mirror images of each other and cam tracks 128, 128a are coaxially mounted with respect to each other and comprise mirror images of each other.

In operation, as drum 82 rotates in the direction of the unmarked arrow in FIG. 6, each position guide arm 124 is constrained to follow the track profile 128' of position cam tracks 128, 128a so that, as best seen in FIG. 6, because of the eccentric configuration of the recessed track profile 128' position guide arm 124 will reciprocate radially with respect to the axis of rotation of central shaft 88. The corresponding radial advance and retraction of each cylinder tube 112 results in advancing each mandrel 102 from its recessed position within its associated mandrel passageway 136 to a radially outwardly extended position as shown in Zone A (FIG. 6). Still referring to FIG. 6, after each mandrel is extended sufficiently radially outwardly of its associated mandrel passageway 136 the eccentric configuration of the recessed track profile 120' of control cam tracks 120, 120a moves control guide arm 116 radially inwardly to impose a radially retracting movement on control bar 110 as shown in Zone B. Referring now to FIGS. 7 and 7A, the radially retracting movement of control bar 110 causes the upper portion 106 of each mandrel 102 to move closer to the bottom portion 108 thereof, thereby expanding, in Zone C (FIG. 6) flexible sidewall member 104 radially outwardly as shown in FIG. 7A.

Control bar 110 is positioned, by virtue of the radially outward configuration of the track profile 120' in Zone A (FIG. 6), to maintain upper portion 106 of mandrel 102 spaced apart its maximum distance from lower portion 108 whereby flexible sidewall member 104 is maintained in its fully longitudinally elongated and radially contracted configuration as shown in Zone A of FIG. 6.

As shown in FIG. 7A, flexible sidewall member 104 is longitudinally compressed and radially expanded by upper portion 106 of mandrel 102 being drawn closer to lower portion 108. This provides the radially expanding folding action on turned-out portion 10a of web 10 (portion 10a is shown in FIG. 7) thereby folding the turned-out portion of fabric and forming hem 10b (as shown in FIG. 7A). As drum 82 continues its rotation the configuration of the track profile 120' again extends radially outwardly to move upper portion 106 of mandrel 102 away from lower portion 108 and thereby longitudinally elongate and radially contract flexible sidewall member 104 as shown in Zone C of FIG. 6. The radial contraction permits retraction of mandrel 102 back into its recessed position within mandrel passageway 136 as shown in Zone D of FIG. 6. The retraction of mandrel 102 is accomplished in Zone C by the radially inwardly extending configuration of that portion of the track profile 128' of position cam tracks 128, 128a. As drum 82 continues its rotation, the cycle is repeated. As with the embodiment of FIGS. 2-4, the provision of a plurality of mandrels enables the formation of a large number of folded hems on a web of material 10 moving rapidly over rotating drum 82.

Referring again to FIG. 1, the hems 10b formed around the periphery of openings 12 are passed between rollers 146 and 147 which may impose additional pressure on hems 10b to help insure securing the hems in place. Web 10 may be cut into discrete pieces either between the hemmed openings 12 or through the openings 12 to provide arcuate hemmed cut-outs in the discrete pieces of material, which are readily useable in the manufacture of disposable diapers and incontinence control garments generally.

The fabric of web 10 may be perforated in a circular pattern around opening 12 to aid hem 10b in lying flat or it may be left unperforated to provide, with certain types of fabric, a contoured profile to the hem which may aid in providing a sealing effect to reduce or prevent leakage in diaper construction.

While the invention has been described in detail with respect to the specific preferred embodiments illustrated, it will be appreciated by those skilled in the art that upon reading and understanding of the foregoing numerous other modifications and embodiments will suggest themselves which other modifications and embodiments are nonetheless within the spirit and scope of the invention and the appended claims.

What is claimed is:

1. A method of forming folded hems about the periphery of respective openings in a moving fabric web by utilizing at least one mandrel having a folding portion thereon including radially expandable and contractible sidewall members wherein the method comprises:

moving a continuous web of resiliently stretchable fabric having a plurality of cut out openings therein into a hemming station;

supporting the fabric web for continuous movement on a fabric support means extending along a curvilinear path having formed therein at least one mandrel passageway of a diameter less than the diameter of respective ones of the openings, positioning the fabric web on said fabric support means with at least one of the openings aligned with the mandrel passageway and mounting the mandrel for orbital movement with said fabric support means to insert and withdraw the mandrel through the mandrel passageway;

placing a hold-down member on the fabric web adjacent the periphery of at least one of the openings to hold the fabric web in place on the fabric support means while inserting the mandrel into the respective openings from one said of the fabric for a distance sufficient to turn out of the web a peripheral portion of the fabric adjacent the respective openings and to align the sidewall member of the mandrel in folding alignment with the turned-out portion;

radially expanding said sidewall members of the thus-aligned folding portion by mechanically flexing said sidewall member sufficiently to fold the turned-out portion of the fabric into contact with the other side of the fabric web to form the hem while placing a guide member associated with the mandrel adjacent the end of the sidewall remote from the fabric and moving said guide member toward the fabric, directing the expanding sidewall member downwardly into pressing engagement with the fabric;

radially contracting said sidewall member and withdrawing the mandrel through the mandrel passageway and the opening aligned therewith; and securing the hem in place by fastening means and withdrawing the moving web from the hemming station.

2. The method of claim 1 wherein said sidewall member includes an inflatable bladder of toroidal configuration extending radially about the periphery of said sidewall and the steps of radially expanding and contracting said sidewall member are accomplished by respectively inflating and deflating the bladder to form a folded hem in the fabric.

3. The method of claim 2 wherein the mandrel has positioning means operatively connected thereto for alternately inserting and withdrawing the mandrel through the mandrel passageway and cam means, respectively associated with said positioning means, said control bar and said lower portion of the mandrel, including the steps of moving said cam means and coordinatedly moving said control bar, expanding and contracting said bladder while alternately inserting and withdrawing the mandrel through the mandrel passageway and the fabric.

4. The method of claim 3 wherein said bladder contains static air or other fluid trapped therein and including the steps of alternately expanding said bladder pneumatically or hydraulically then contracting said bladder by cooperation thereof with said control bar.

5. The method of claim 1 wherein said fastening means comprises an adhesive and including the steps of applying an adhesive to that portion of the fabric which is pressed together to form the hem.

6. The method of claim 1 wherein said resiliently stretchable web of fabric comprises a material utilizable in a disposable garment, and including the additional step of cutting the continuous web of fabric into individual pieces having thereon hemmed openings or segments thereof and making disposable garments therefrom.

7. Apparatus for forming a folded hem about the periphery of an opening in a fabric web comprises:

a mandrel having an upper portion, a lower portion and a radially expandable and contractible sidewall member of the mandrel connecting the upper and lower portions thereof and a central mechanism including a control bar affixed to the upper portion of the mandrel and operatively connected to a control guide arm having thereon a cam follower which engages a control cam track which defines the travel path of the control bar, the control cam track being of eccentric configuration whereby during each revolution of the drum the control guide arm guides the control bar to alternately move the upper and lower portions of the mandrel axially toward and away from each other whereby to alternately radially expand the sidewall member when on the fabric side of the drum and contract the sidewall member for movement back through the mandrel passageway at least once during each revolution of the drum;

mandrel support means on which the mandrel is mounted;

a rotating fabric support drum for carrying a continuous web of the fabric of said drum having a fabric side dimensioned and configured to receive and support a fabric thereon, including at least one mandrel passageway dimensioned and configured to permit passage therethrough of at least so much of the mandrel as is necessary to position the mandrel for forming a folded hem in the fabric, the mandrel being mounted by the mandrel support means for orbiting with the rotating drum to maintain the mandrel in axial alignment with the mandrel passageway for at least a segment of each revolution of the drum;

positioning means operatively connected to the mandrel for moving the mandrel relative to the drum, reciprocatingly inserting and withdrawing the mandrel through the mandrel passageway and between (i) a folding alignment position in which the sidewall member is on the fabric side of the fabric support drum, and (ii) a withdrawn position in which the mandrel is clear of at least the fabric side of the fabric support drum.

8. The apparatus of claim 7 wherein the sidewall member comprises an inflatable bladder of toroidal configuration extending radially about the periphery of the sidewall and the control mechanism further includes pressurizing means for selectively forcing a fluid into and withdrawing the fluid from the bladder to alternately radially expand and contract the bladder at least once during each revolution of the drum.

9. Apparatus for forming a folded hem about the periphery of an opening in a fabric web comprises:

a mandrel having an upper portion, a sidewall comprising a radially expandable and contractible fabric folding means, and a lower portion;

mandrel support means on which the mandrel is mounted;

fabric support means having a fabric side dimensioned and configured to receive and support a fabric thereon, and further having therein at least one mandrel passageway dimensioned and configured to permit passage therethrough of at least so much of the mandrel as is necessary to position the mandrel for forming a folded hem in the fabric;

a positioning mechanism including a positioning bar affixed to the mandrel and operatively connected to a position guide arm having thereon a cam follower which engages a position cam track which defines the travel path of the positioning mechanism, the position cam track being of eccentric configuration whereby during each revolution of the drum the position guide arm guides the positioning bar to reciprocatingly insert and withdraw the mandrel through the mandrel passageway and between (i) a folding alignment position in which the folding means is on the fabric side of the fabric support means, and (ii) a withdrawn position in which the mandrel is clear of at least the fabric side of the fabric support means; and control means operatively connected to the folding means to radially expand the folding means to its expanded position when it is on the fabric side of the support means and to radially contract it for movement through the mandrel passageway.

10. The apparatus of claim 9 wherein the fabric folding means comprises an expandable and contractible sidewall member of the mandrel connecting the upper and lower portions thereof and the control means comprises a control bar affixed to the upper portion of the mandrel and operatively connected to a control guide arm having thereon a cam follower which engages a control cam track which defines the travel path of the control bar, the control cam track being of eccentric configuration whereby during each revolution of the drum the control guide arm guides the control bar to alternately move the upper and lower portions of the mandrel axially toward and away from each other whereby to alternately radially expand and contract the sidewall member.

11. The apparatus of claim 10 wherein the fabric folding means further comprises an inflatable bladder of toroidal configuration extending radially about the periphery of the sidewall, the control means selectively forcing a fluid into the withdrawing same from the bladder, alternately radially expanding and contracting the bladder as the mandrel is alternately inserted and withdrawn from the mandrel passageway.

12. The apparatus of claim 11 wherein the fabric support means comprises a rotating drum with the mandrel being mounted by the mandrel support means for orbiting with the drum to maintain the mandrel in axial alignment with the mandrel passageway for at least a segment of each revolution of the drum.

13. Apparatus for forming a folded hem about the periphery of an opening in a fabric web comprises:

a mandrel having an upper portion, a sidewall comprising a radially expandable and contractible fabric folding means, and a lower portion;

mandrel support means on which the mandrel is mounted;

a rotating fabric support drum for carrying a continuous web of fabric thereon, the mandrel support means mounting the mandrel for orbiting with said rotating drum to maintain the mandrel in axial alignment with the mandrel passageway for at least a segment of each revolution of the drum, said support drum having a fabric side dimensioned and configured to receive and support a stretchable disposable fabric thereon, and further having therein at least one mandrel passageway dimensioned and configured to permit passage therethrough of at least so much of the mandrel as is necessary to position the mandrel for forming hem in the web opening;

positioning means operatively connected to the mandrel to reciprocatingly insert and withdraw the mandrel through the mandrel passageway and between (i) a folding alignment position in which the folding means is on the fabric side of the fabric support means, and (ii) a withdrawn position in which the mandrel is clear of at least the fabric side of the fabric support means; and control means operatively connected to the folding means to radially expand the folding means to its expanded position when it is on the fabric side of the support means and to radially contract it for movement through the mandrel passageway.

14. The apparatus of claim 11 wherein the fabric folding means comprises an expandable and contractible sidewall member of the mandrel connecting the upper and lower portions thereof and the control means comprises a control bar affixed to the upper portion of the mandrel and operatively connected to a control guide arm having thereon a cam follower which engages a control cam track which defines the travel path of the control bar, the control cam track being of eccentric configuration whereby during each revolution of the drum the control guide arm guides the control bar to alternately move the upper and lower portions of the mandrel axially toward and away from each other whereby to alternately radially expand and contract the sidewall member at least once during each revolution of the drum.

15. The apparatus of claim 13 wherein the fabric folding means comprises an inflatable bladder of toroidal configuration extending radially about the periphery of the sidewall and the control means comprises means to selectively force a fluid into and withdraw it from the bladder whereby to alternately radially expand and contract the bladder at least once during each revolution of the drum.

16. The apparatus of claim 13 wherein the fabric folding means comprises an expandable and contractible sidewall member of the mandrel connecting the upper and lower portions thereof and the control means comprises means to alternately move the upper and lower portions axially toward and away from each other whereby to alternately radially expand and contract the sidewall member.

17. The apparatus of claim 13 wherein the positioning means comprises a positioning bar affixed to the mandrel and operatively connected to a position guide arm having thereon a cam follower which engages a position cam track which defines the travel path of the positioning means, the position cam track being of eccentric configuration whereby during each revolution of the drum the position guide arm guides the positioning bar to reciprocatingly insert and withdraw the mandrel through the mandrel passageway.

18. The apparatus of claim 13 wherein the fabric folding means comprises an expandable and contractible sidewall member of the mandrel connecting the upper and lower portions thereof and the control means comprises a control bar affixed to the upper portion of the mandrel and operatively connected to a control guide arm having thereon a cam follower which engages a control cam track which defines the travel path of the control bar, the control cam track being of eccentric configuration whereby during each revolution of the drum the control guide arm guides the control bar to alternately move the upper and lower portions of the mandrel axially toward and away from each other whereby to alternately radially expand and contract the sidewall member.

* * * * *